US012691126B2

(12) United States Patent
Ko et al.

(10) Patent No.: US 12,691,126 B2
(45) Date of Patent: Jul. 28, 2026

(54) NON-SURGICAL PREVENTION OF UNPLEASANT ODOR IN MEATS AND AGGRESSIVE OR SEXUAL BEHAVIOR IN MALE RUMINANTS

(71) Applicant: Insigna Inc., Champaign, IL (US)

(72) Inventors: CheMyong Ko, Champaign, IL (US); ChanJin Park, Savoy, IL (US); Rex Allen Hess, Champaign, IL (US); Po-Ching Patrick Lin, Champaign, IL (US)

(73) Assignee: Insigna Inc., Champaign, IL (US)

( * ) Notice: Subject to any disclaimer, the term of this patent is extended or adjusted under 35 U.S.C. 154(b) by 444 days.

(21) Appl. No.: 18/324,798

(22) Filed: May 26, 2023

(65) Prior Publication Data

US 2023/0381199 A1 Nov. 30, 2023

Related U.S. Application Data

(63) Continuation-in-part of application No. 17/937,740, filed on Oct. 3, 2022, now Pat. No. 11,938,140.

(60) Provisional application No. 63/378,227, filed on Oct. 3, 2022, provisional application No. 63/365,389, filed on May 26, 2022.

(51) Int. Cl.

| | |
|---|---|
| *C07J 1/00* | (2006.01) |
| *A61K 9/00* | (2006.01) |
| *A61K 31/565* | (2006.01) |
| *A61K 31/568* | (2006.01) |
| *A61K 31/573* | (2006.01) |
| *A61P 5/08* | (2006.01) |
| *A61P 5/26* | (2006.01) |
| *A61P 5/28* | (2006.01) |
| *A61P 5/30* | (2006.01) |

(52) U.S. Cl.
CPC .......... *A61K 31/565* (2013.01); *A61K 9/0019* (2013.01); *A61K 31/573* (2013.01); *A61P 5/08* (2018.01); *A61P 5/28* (2018.01)

(58) Field of Classification Search
CPC . C07J 1/00; A61K 9/00; A61K 31/565; A61K 31/568; A61P 5/26; A61P 5/30
See application file for complete search history.

(56) References Cited

U.S. PATENT DOCUMENTS

| | | |
|---|---|---|
| 3,991,750 A | 11/1976 | Vickery |
| 4,096,239 A | 6/1978 | Katz et al. |
| 4,123,519 A | 10/1978 | Tribble et al. |
| 4,210,644 A | 7/1980 | Desjardins et al. |
| 4,610,687 A | 9/1986 | Fogwell |
| 5,035,891 A | 7/1991 | Runkel et al. |
| 5,314,882 A | 5/1994 | Pantic et al. |
| 6,063,395 A | 5/2000 | Markkula et al. |
| 6,458,387 B1 | 10/2002 | Scott et al. |
| 7,589,082 B2 | 9/2009 | Savoir et al. |
| 11,135,229 B2 | 10/2021 | Ko |
| 11,938,140 B2 | 3/2024 | Ko et al. |
| 2011/0112475 A1 | 5/2011 | Benson |
| 2017/0258808 A9 | 9/2017 | Yoakum et al. |
| 2020/0171047 A1 | 6/2020 | Ko |
| 2020/0171048 A1 | 6/2020 | Ko |
| 2022/0370474 A1 | 11/2022 | Ko |
| 2023/0381197 A1 | 11/2023 | Ko et al. |
| 2023/0381198 A1 | 11/2023 | Ko et al. |
| 2023/0381200 A1 | 11/2023 | Ko et al. |
| 2024/0180926 A1 | 6/2024 | Ko et al. |
| 2026/0076978 A1 | 3/2026 | Ko et al. |

FOREIGN PATENT DOCUMENTS

| | | |
|---|---|---|
| CN | C/CN-113423391 A | 9/2021 |
| GB | 636908 A | 5/1950 |
| WO | WO-2020112180 A1 | 6/2020 |
| WO | 2023230607 | 11/2023 |
| WO | 2023230619 | 11/2023 |
| WO | 2023230621 | 11/2023 |
| WO | 2024076995 | 4/2024 |

OTHER PUBLICATIONS

U.S. Appl. No. 18/437,978, filed Feb. 9, 2024, Non-Surgical Prevention of Boar Taint and Aggressive Behavior.
"U.S. Appl. No. 16/526,874, 312 Amendment filed Jul. 8, 2021", 3 pgs.
"U.S. Appl. No. 16/526,874, Advisory Action mailed Sep. 9, 2020", 5 pgs.
"U.S. Appl. No. 16/526,874, Examiner Interview Summary mailed Jun. 1, 2021", 3 pgs.

(Continued)

*Primary Examiner* — Brenda L Coleman
(74) *Attorney, Agent, or Firm* — Schwegman Lundberg & Woessner, P.A.

(57) ABSTRACT

Embodiments of the present invention provide a pharmaceutical intervention in the neonatal to infantile ruminants that inhibits the activation of the HPG axis, growth of the testis and inhibits testicular production of testosterone, which prevent the development of aggressive behavior in the maturing males and the presence of male-specific odor in the meat. The invention comprises treatment with an estrogen or a combination of an estrogen and an androgen in the newborn males using extended drug delivery methods, with a defined duration of no more than 1-4 months or infantile period of growth, for the purpose of inhibiting the production of testosterone and the accumulation of male-specific odor. The drug delivery component may consist of biocompatible-/biodegradable polymers in the form of pellets, microspheres, or gels, or in solvents or solutions (hereafter, drug complex). The invention embodies neonatal/infantile period treatment with a drug complex consisting of a hormone-based compound configured to inhibit development and function of hypothalamic Kisspeptin neurons, pituitary release of luteinizing hormone and postnatal development of the testis through the use of sustained but temporary release of the compounds into the body of an animal once the drug-carrier has been injected or implanted therein.

12 Claims, 2 Drawing Sheets

(56)         References Cited

OTHER PUBLICATIONS

"U.S. Appl. No. 16/526,874, Final Office Action mailed Apr. 26, 2021", 8 pgs.

"U.S. Appl. No. 16/526,874, Final Office Action mailed Jun. 9, 2020", 10 pgs.

"U.S. Appl. No. 16/526,874, Non Final Office Action mailed Nov. 24, 2020", 8 pgs.

"U.S. Appl. No. 16/526,874, Non Final Office Action mailed Dec. 11, 2019", 6 pgs.

"U.S. Appl. No. 16/526,874, Notice of Allowability mailed Aug. 30, 2021", 5 pgs.

"U.S. Appl. No. 16/526,874, Notice of Allowance mailed Jul. 2, 2021", 8 pgs.

"U.S. Appl. No. 16/526,874, Response filed Feb. 16, 2021 to Non Final Office Action mailed Nov. 24, 2020", 7 pgs.

"U.S. Appl. No. 16/526,874, Response filed Mar. 10, 2020 to Non Final Office Action mailed Dec. 11, 2019", 7 pgs.

"U.S. Appl. No. 16/526,874, Response filed Jun. 9, 2021 to Final Office Action mailed Apr. 26, 2021", 7 pgs.

"U.S. Appl. No. 16/526,874, Response filed Aug. 17, 2020 to Final Office Action mailed Jun. 9, 2020", 8 pgs.

"U.S. Appl. No. 16/526,874, Response filed Oct. 9, 2020 to Advisory Action mailed Sep. 9, 2020", 10 pgs.

"U.S. Appl. No. 16/699,307, Final Office Action mailed Jan. 11, 2021", 12 pgs.

"U.S. Appl. No. 16/699,307, Non Final Office Action mailed May 12, 2020", 7 pgs.

"U.S. Appl. No. 16/699,307, Non Final Office Action mailed Jun. 28, 2021", 16 pgs.

"U.S. Appl. No. 16/699,307, Response filed Apr. 12, 2021 to Final Office Action mailed Jan. 11, 2021", 11 pgs.

"U.S. Appl. No. 16/699,307, Response filed Nov. 12, 2020 to Non Final Office Action mailed May 12, 2020", 8 pgs.

"U.S. Appl. No. 17/646,207, Non Final Office Action mailed Mar. 30, 2023", 9 pgs.

"U.S. Appl. No. 17/646,207, Preliminary Amendment filed Aug. 15, 2022", 5 pgs.

"U.S. Appl. No. 17/937,740, Final Office Action mailed Oct. 30, 2023", 6 pgs.

"U.S. Appl. No. 17/937,740, Non Final Office Action mailed Jul. 28, 2023", 5 pgs.

"U.S. Appl. No. 17/937,740, Response filed Oct. 13, 2023 to Non Final Office Action mailed Jul. 28, 2023", 5 pgs.

"U.S. Appl. No. 17/937,743, Final Office Action mailed Oct. 12, 2023", 17 pgs.

"U.S. Appl. No. 17/937,743, Non Final Office Action mailed Feb. 16, 2023".

"U.S. Appl. No. 17/937,743, Non Final Office Action mailed Jun. 8, 2023", 12 pgs.

"U.S. Appl. No. 17/937,743, Response filed Jan. 11, 2023 to Restriction Requirement mailed Jan. 5, 2023", 6 pgs.

"U.S. Appl. No. 17/937,743, Response filed May 16, 2023 to Non Final Office Action mailed Feb. 16, 2023", 6 pgs.

"U.S. Appl. No. 17/937,743, Response filed Sep. 8, 2023 to Non Final Office Action mailed Jun. 8, 2023", 10 pgs.

"U.S. Appl. No. 17/937,743, Restriction Requirement mailed Jan. 5, 2023".

"U.S. Appl. No. 18/099,654, Preliminary Amendment filed Apr. 10, 2023", 9 pgs.

"Chinese Application Serial No. 201980089378.4, Office Action mailed Apr. 12, 2023", w/ English Translation, 11 pgs.

"Chinese Application Serial No. 201980089378.4, Office Action mailed Aug. 29, 2022", w/English translation, 18 pgs.

"Chinese Application Serial No. 201980089378.4, Response Filed Jan. 13, 2023 to Office Action mailed Aug. 29, 2022", W/ English Claims, 13 pgs.

"Claims of copending U.S. Appl. No. 17/937,740", (Oct. 3, 2022), 2 pgs.

"European Application Serial No. 19891161.2, Extended European Search Report mailed Jul. 15, 2022", 9 pgs.

"European Application Serial No. 19891161.2, Response Filed Jan. 10, 2023 to Extended European Search Report mailed Jul. 15, 2022", 10 pgs.

"Guide to the care and use of experimental animals", Canadian Council on Animal Care, p. 371,Atomic Energy Press, vol. 1, (1993), 300 pgs.

"International Application Serial No. PCT/US2019/044230,International Preliminary Report on Patentability mailed Jun. 10, 2021", 6 pgs.

"International Application Serial No. PCT/US2019/044230, International Search Report mailed Oct. 29, 2019", 2 pgs.

"International Application Serial No. PCT/US2019/044230, Written Opinion mailed Oct. 29, 2019", 4 pgs.

"International Application Serial No. PCT/US2023/067550, International Search Report mailed Aug. 10, 2023", 2 pgs.

"International Application Serial No. PCT/US2023/067550, Written Opinion mailed Aug. 10, 2023", 4 pgs.

"International Application Serial No. PCT/US2023/067565, Internation Search Report mailed Sep. 27, 2023", 4 pgs.

"International Application Serial No. PCT/US2023/067565, Written Opinion mailed Sep. 27, 2023", 4 pgs.

"International Application Serial No. PCT/US2023/067568, International Search Report mailed Sep. 29, 2023", 3 pgs.

"International Application Serial No. PCT/US2023/067568, Written Opinion mailed Sep. 29, 2023", 4 pgs.

Aldal, Inghild, et al., "Levels of androstenone and skatole and the occurrence of boar taint in fat from young boars", Livestock Production Science, 95(1), (2005), 121-129.

Andresen, Øystein, et al., "Boar taint related compunds: Androstenone/Skatole/other substances", Acta Veterinaria Scandinavica, 48(Suppl 1):S5, (2006), 4 pgs.

Atanassova, N, et al., "Permanent Effects of Neonatal Estrogen Exposure in Rats on Reproductive Hormone Levels, Sertoli Cell Number, and the Efficiency of Spermatogenesis in Adulthood", Endocrinology, 140(11), (1999), 5364-5373.

At-Taras, Eeman E, et al., "Reducing Estrogen Synthesis in Developing Boars Increases Testis Size and Total Sperm Production", Journal of Andrology, 27(4), (2006), 552-559.

Berger, T, et al., "Increased testicular estradiol during the neonatal interval reduces Sertoli cell numbers", Anim Reprod Sci. 2018;189:146-51., (2018), 146-151.

Bonneau, Michel, et al., "An international study on the importance of androstenone and skatole for boar taint: I. Presentation of the programme and measurement of boar taint compounds with different analytical procedures", Meat Science, 54(3), (2000), 251-259.

Bonneau, Michel, et al., "Pros and Cons of Alternatives to Piglet Castration: Welfare, Boar Taint, and Other Meat Quality Traits", Animals, 9(11), 884, (2019), 12 pgs.

Candek-Potokar, Marjeta, et al., "Alternatives to surgical castration in pigs", Životnov'dni nauki, 52(5): 41-51, (2015), 13 pgs.

Cortes, ME et al., "The Role of Kisspeptin in the Onset of Puberty and in the Ovulatory Mechanism: a Mini-review", J Pediatr Adolesc Gynecol., 28(5), (2015), 286-291.

D'Anglemont De Tassigny, Xavier, et al., "Hypogonadotropic hypogonadism in mice lacking a functional Kiss1 gene", PNAS, 105(25), (2007), 10714-10719.

Daxenberger, A, et al., "Suppression of androstenone in entire male pigs by anabolic preparations", Livestock Production Science, 69(2), (2001), 139-144.

Garcia-Regueiro, JA, et al., "Evaluation of the contribution of skatole, indole, androstenone and androstenols to boar-taint in back fat of pigs by HPLC and capillary gas chromatography (CGC)", Meat Science, 25(4),, (1989), 307-316.

Gettys, T. W, et al., "Suppression of LH secretion by oestradiol, dihydrotestosterone and trenbolone acetate in the acutely castrated bull", J Endocrinol., 100(1), (1984), 107-112.

Gorski, R A, "Modification of ovulatory mechanisms by postnatal administration of estrogen to the rat", American Journal of Physiology, vol. 205, No. 5, (1963), 842-844.

(56)            References Cited

OTHER PUBLICATIONS

Grindflek, E, et al., "Revealing genetic relationships between compounds affecting boar taint and reproduction in pigs", Journal of Animal Science, 89(3), (2011), 680-92.

Hayashi, S, "Sterilization of Female Rats by Neonatal Placement of Estradiol Micropellets in anterior Hypothalamus", Endocrinol. Japan, vol. 23, No. 1, (1976), 55-60.

Hess, Rex A, et al., "Estrogens and development of the rete testis, efferent ductules, epididymis and vas deferens", Differentiation 118, (2021), 41-71.

Kind, Fred A, et al., "Inhibition of sexual development in male and female rats treated with various steroids at the age of five days", Acta Endocrinogica vol. 49, No. 2, (Jun. 30, 1965), 193-206.

López-Bote, C, et al., "The reduction of boar taint in male pigs by neonatal testosterone administration", Meat Science, 22(3), (1988), 163-171.

López-Bote, C, et al., "Trenbolone Acetate Induced Changes in the Genital Tract of Male Pigs", Journal of Veterinary Medicine, Series B, 41(1-10), (1994), 42-48.

Shiori, et al., "Long-Term Neonatal Estrogen Exposure Causes Irreversible Inhibition of LH Pulses by Suppressing Arcuate Kisspeptin Expression via Estrogen Receptors a and b in Female Rodents", Endocrinology, 158(9), (2017), 2918-2929.

Minabe, Shiori, "Neonatal Estrogen Causes Irreversible Male Infertility via Specific Suppressive Action on Hypothalamic Kiss1 Neurons", Endocrinology, 160(5), (2019), 1223-1233.

Novaira, Horacio J, et al., "Disrupted Kisspeptin Signaling in GnRH Neurons Leads to Hypogonadotrophic Hypogonadism", Mol Endocrinol, 28(2), (2014), 225-238.

Pantic, V., et al., "Testicular Structure and Serum Concentration of Gonadal Steroids in Male Pigs Neonatally Castrated or Treated with Estradiol and Progesterone", Bulletin de l'Academie Serbe des Sciences etdes Arts Classe des Sciences Naturelles et Mathematiques: Science Naturelles, vol. 25, pp. 57-72, (1984), 57-72.

Rasmussen, Martin, et al., "Regulation of Porcine Hepatic Cytochrome P450—Implication for Boar Taint", Comput Struct Biotechnol J., 11(19), (2014), 106-112.

Rosa-E-Silva, Alzira, et al., "Prepubertal Administration of Estradiol Valerate Disrupts Cyclicity and Leads to Cystic Ovarian Morphology during Adult Life in the Rat: Role of Sympathetic Innervation", Endocrinology, 144(10), (2003), 4289-4297.

Sheridan, PJ, et al., "The effect of anabolic agents on growth rate and reproductive organs of pigs", Livestock Production Science, 26(4), (1990), 263-275.

Stewart, Lawton, "Implanting Beef Cattle", UGA Cooperative Extension Bulletin 1302, (2013), 8 pgs.

Uenoyama, Yoshihisa, et al., "Central Mechanism Controlling Pubertal Onset in Mammals: a Triggering Role of Kisspeptin", Front Endocrinol (Lausanne), 10:312, (2019), 12 pgs.

Ventanas, J, et al., "Testicular development, androstenone levels and androstenone odour of untreated and trenbolone implanted boars", Journal of the Science of Food and Agriculture, 57(1), (1991), 127-133.

Williamson, DE, et al., "A selective immunization procedure against 5a-androstenone in boars", Animal Science, 35(3), (1982), 353-360.

Zamaratskaia, G, et al., "Plasma skatole and androstenone levels in entire male pigs and relationship between boar taint compounds, sex steroids and thyroxine at various ages", Livestock Production Science, 87(2), (2007), 91-98.

"U.S. Appl. No. 17/937,740, Response filed Nov. 17, 2023 to Final Office Action mailed Oct. 30, 2023", 4 pgs.

"U.S. Appl. No. 17/937,740, Notice of Allowance mailed Dec. 6, 2023", 5 pgs.

"U.S. Appl. No. 17/937,740, 312 Amendment filed Dec. 12, 2023", 5 pgs.

"U.S. Appl. No. 17/937,740, PTO Response to Rule 312 Communication mailed Dec. 27, 2023", 2 pgs.

"U.S. Appl. No. 17/937,743, Response filed Jan. 3, 2024 to Final Office Action mailed Oct. 12, 2023", 7 pgs.

"International Application Serial No. PCT US2023 075842, Invitation to Pay Additional Fees mailed Jan. 23, 2024", 12 pgs.

"U.S. Appl. No. 17/937,743, Advisory Action mailed Jan. 19, 2024", 3 pgs.

"International Application Serial No. PCT US2023 075842, International Search Report mailed Mar. 15, 2024", 5 pgs.

"International Application Serial No. PCT US2023 075842, Written Opinion mailed Mar. 15, 2024", 11 pgs.

"U.S. Appl. No. 17/937,743, Non Final Office Action mailed Jul. 5, 2024", 25 pgs.

"U.S. Appl. No. 17/937,743, Response filed Dec. 5, 2024 to Non Final Office Action mailed Jul. 5, 2024", 9 pgs.

"International Application Serial No. PCT US2023 067550, International Preliminary Report on Patentability mailed Dec. 5, 2024", 6 pgs.

"International Application Serial No. PCT US2023 067568, International Preliminary Report on Patentability mailed Dec. 5, 2024", 6 pgs.

Rebourcet, Diane, "Sertoli Cells Maintain Leydig Cell Number and Peritubular Myoid Cell Activity in the Adult Mouse Testis", PLoS One, vol. 9, Issue 8, (2014), 13 pages.

"U.S. Appl. No. 17/937,743, Final Office Action mailed Mar. 19, 2025", 25 pgs.

"U.S. Appl. No. 18/437,978, Non Final Office Action mailed Nov. 17, 2025", 4 pgs.

"U.S. Appl. No. 19/334,213, Preliminary Amendment filed Dec. 8, 2025", 5 pgs.

"U.S. Appl. No. 18/324,786, Non Final Office Action mailed Nov. 17, 2025", 6 pgs.

"Brazilian Application Serial No. 1120240245314, Office Action mailed Mar. 9, 2025", w/ Machine English Translation, 2 pg.

"Brazilian Application Serial No. 1120240245314, Response Filed May 16, 2025 to Office Action mailed Mar. 9, 2025", w/ Machine English Translation, 11 pgs.

"International Application Serial No. PCT/US2023/067565, International Preliminary Report on Patentability mailed Dec. 5, 2024", 6 pgs.

"International Application Serial No. PCT/US2023/075842, International Preliminary Report on Patentability mailed Apr. 17, 2025", 13 pgs.

"Korean Application Serial No. 10-2024-7042762, Notice of Preliminary Rejection mailed Dec. 27, 2024", w/ English Translation, 6 pgs.

"Korean Application Serial No. 10-2024-7042763, Office Action mailed Dec. 27, 2024", w/ English Translation, 6 pgs.

"U.S. Appl. No. 18/437,978, Response filed Feb. 16, 2026 to Non Final Office Action mailed Nov. 17, 2025", 8 pgs.

"U.S. Appl. No. 18/324,786, Response filed Feb. 16, 2026 to Non Final Office Action mailed Nov. 17, 2025", 7 pgs.

"European Application Serial No. 23812819.3, Extended European Search Report mailed Feb. 25, 2026", 10 pgs.

"European Application Serial No. 23812820.1, Extended European Search Report mailed Feb. 25, 2026", 11 pgs.

Allrich, R. D, "Symposium Estrus, New Devices, and Monitoring Endocrine and Neural Control of Estrus In Dairy Cows 1", [Online]. Retrieved from the InternetURL http dx.doi.org https doi.org 10.3168 jds. S0022-03029477216-7, Sep. 1, 1994, 2738-2744.

Habert, "Effets des estrogenes sur le développement du testicule pendant la vie foetale et neonatale", Gynecologie Obstetrique and Fertilite, Elsevier Masson, FR, vol. 34, No. 10, With Machine English Translation, Oct. 1, 2006, 16 pgs.

Heitzman, R J, "The Effectiveness of Anabolic Agents in Increasing Rate of Growth in Farm Animals Report on Experiments in Cattle", Environmental Quality And Safety. Supplement, Thieme, Stuttgart, DE, No. 5, Jan. 1, 1976, 10 pgs.

Reynolds, "The effect of trenbolone acetate on the bovine oestrous cycle", Animal Reproduction Science., vol. 4, No. 2 URL https www.sciencedirect.com science article abs pii 0378432081900373, Oct. 1, 1981, 10 pages.

NON-SURGICAL PREVENTION OF UNPLEASANT ODOR IN MEATS AND AGGRESSIVE OR SEXUAL BEHAVIOR IN MALE RUMINANTS

CROSS-REFERENCE TO RELATED APPLICATIONS

This application claims priority and the benefit of U.S. application Ser. No. 17/937,740, filed Oct. 3, 2022 and U.S. Provisional Appl. Ser. Nos. 63/365,389 and 63/378,227, filed May 26, 2022 and Oct. 3, 2022, respectively, which are incorporated by reference as if fully set forth herein.

BACKGROUND

Surgical castration is a medical procedure that is routinely performed on nearly all male meat production animals as a method of decrease male's gonadal sex hormone. Generally, male ruminants with intact gonads cause negative issues with handling, management, carcass yield and meat quality (1, 2, 3, 4). Working with intact male ruminants can be dangerous to both the handler and the animal; therefore, it is preferable to castrate the males at an early age (3). On the farm, intact males have to be isolated from females to prevent unintentional breeding. The males are also isolated from other males due to their aggressive and/or sexual behavior, which increases the complexity and cost of animal management. The cause of these unwanted animal behaviors is due to the presence of androgen hormones (1, 5, 6, 7); thus, the primary purpose of castration in male livestock is to remove the source of androgen production, the testes.

Aggressive behavior. To prevent breeding and to reduce aggressive behavior in the ruminant species, castration of the males is performed as routine animal husbandry (5). Recently, immunocastration has been introduced, as it will reduce sexual behavior and mounting frequencies, similar to castration (4, 8, 9, 10). If the bulls have had sexual experience, castration does not decrease the mounting behavior (11), but in general, castration decreases this behavior, as evidenced by the fact that Testosterone (T) treatment will restore it (12).

Male-specific odor and meat quality. It is well-established that androgen production in male pigs results in a pungent, urine-like odor in the cooked meat, which is called 'boar taint' (13, 14). Male-specific odors are also associated with other species, including ruminants. For example, musk odor from the musk glands especially in musk deer is well-known for its role as a pheromone (15, 16, 17). Other volatile compounds are also found in the fat and meat of ruminants and, as with boar taint, musk odors are controlled by androgen production and contribute to the reasons established for routine castration of male livestock (3, 18, 19, 20, 21, 22, 23, 24, 25, 26, 27).

There are three current methods of castration in male ruminants: physical, chemical, and immune castration. Physical methods include surgical removal of the testicles, application of a constricting elastic band (rubber ring) at the base of the scrotum (28), and use of external clamping with a specialized device such as the Burdizzo clamp (29). Chemical castration includes the injection of sclerosing or toxic agents (e.g. 88% lactic acid) into the testicular parenchyma to cause irreparable damage and loss of function (30). Chemical castration requires additional procedural time and technical skill, and almost twice the healing time compared with surgical castration (30). The immunocastration method requires the injection of an immunocontraceptive formulation (1, 31) that will induce antibody production against gonadotropin releasing hormone (GnRH), which results in decreased productions of endogenous pituitary and gonadal hormones (32).

The immunocontraceptive method, while effective, presents some notable challenges and management problems. For instance, in bulls the contraceptive formula must be injected into males older than 2-months and requires repeated injections to ensure continued infertility. Thus, just to inject the immunocontraceptives, workers must handle large animals weighing several hundreds of kilograms. Similarly, in male pigs, the first injection is typically required when the animals are 9 to 13-weeks-old, weighing between 30-50 kg. This exposes farm workers to undue safety risks associated with handling aggressive, large animals, while handling a sharp instrument. Accidental exposure of workers to the immunocontraceptive is a serious safety risk. Another drawback to the use of immunocastration is that the treated animals cannot be sold in the market immediately after the last injection due to concerns about residual drugs being present in the meat.

SUMMARY

One embodiment provides a method for inhibiting testicular development in ruminants, which prevents the pubertal rise in blood and tissue androgens, and in particular testosterone, the major hormone responsible for aggressive/sexual behavior and male-specific odor, comprising of injecting in said ruminants an estrogen or a combination of an estrogen and an androgen during the neonatal/infantile period of growth of said male ruminants. In one embodiment, the injection is either subcutaneous or intra-muscular.

One embodiment further comprises an implant wherein the implant comprises said estrogen or a combination of an estrogen and androgen, wherein the estrogen and androgen target hypothalamus-pituitary axis and testis development.

In one embodiment, the implant comprises a material or enclosure that maintains elevated circulating levels of compounds over the neonatal/infantile period of growth. In one embodiment, the material or enclosure that provides sustained release consists with biodegradable polymers or biocompatible materials. In one embodiment, the material or enclosure that provides sustained release is a form of capsule, pellet, microsphere, nanoparticle, gel, or solution.

In another embodiment, the injected synthetic estrogen and androgen are not present in the blood or tissues when the animals are slaughtered.

In one embodiment, the estrogen comprises natural or synthetic estrogenic compounds including estradiol esters such as estradiol benzoate (EB), estradiol valerate, estradiol cypionate, etc. In one embodiment, the dose range of 1-30 mg/kg bodyweight.

In another embodiment, the androgen comprises testosterone, testosterone esters, testosterone metabolites such as $5\alpha$-dihydrotestosterone or their esters, trenbolone or trenbolone esters, or equivalents that have potent androgen activity. In one embodiment, the dose range of 50-200 mg/kg bodyweight.

One embodiment provides that the injected amount of the estrogen and estrogen/androgen combination is in a dose sufficient to inhibit the development of Kisspeptin neurons in the hypothalamus, LH production in the pituitary, proliferation of Sertoli and Leydig cells in the testis and production of androgens in the testis and accumulation of male-specific odor in the fat.

BRIEF DESCRIPTION OF THE DRAWINGS

The drawings illustrate generally, by way of example but not by way of limitation, various embodiments discussed in the present document. In the drawings, which are not necessarily drawn to scale, like numerals may describe similar components in different views. Like numerals having different letter suffixes may represent different instances of similar components.

DETAILED DESCRIPTION

Figure 1:
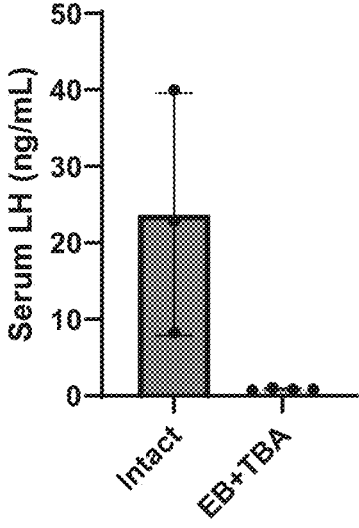
FIG. 1 illustrates exemplary serum LH concentration data from two male subject groups (Intact and EB+TBA) at 3 weeks of age in pigs.
Figure 2:
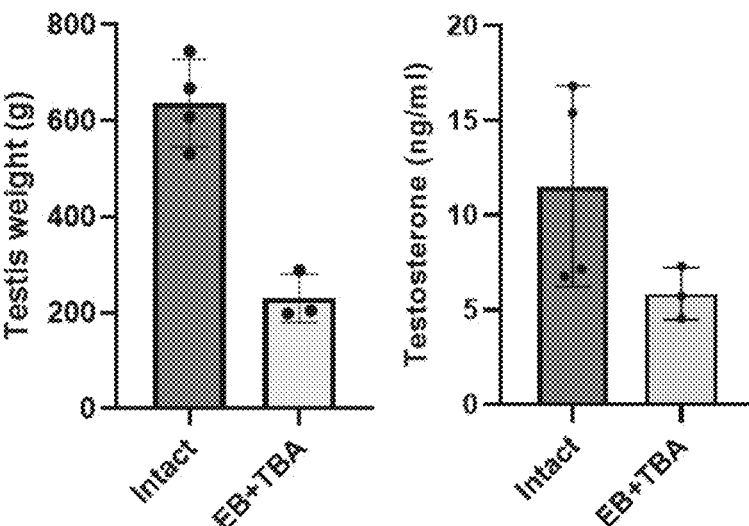
FIG. 2 illustrates exemplary testis weight and serum testosterone level data from two male subject groups (Intact and EB+TBA) at 26 weeks of age in pigs.
Figure 3:
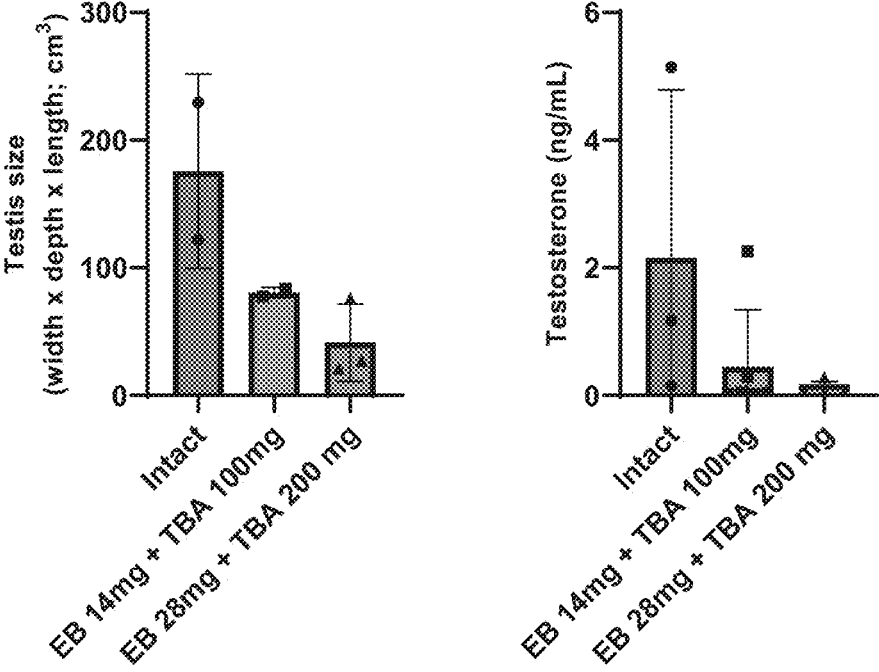
FIG. 3 illustrates exemplary testis size (left) at 3-5 months of age and serum testosterone level (right) at 4-5 months of age data from three subject groups in male goats.

The following detailed description includes references to the accompanying drawings, which form a part of the detailed description. The drawings show, by way of illustration, specific embodiments in which the invention may be practiced. These embodiments, which may also be referred to herein as "examples," are described in enough detail to enable those skilled in the art to practice the invention. The example embodiments may be combined, other embodiments may be used, or structural, and logical changes may be made without departing from the scope of the present invention. While the disclosed subject matter will be described in conjunction with the enumerated claims, it will be understood that the exemplified subject matter is not intended to limit the claims to the disclosed subject matter. The following detailed description is, therefore, not to be taken in a limiting sense, and the scope of the present invention is defined by the appended claims and their equivalents.

The present invention pertains generally to preventing development of the testis in ruminants, production and accumulation of the molecules that cause or contribute to male-specific odor, and androgen-induced aggressive and sexual behavior in males with age. Specifically, the invention relates to the inhibition of functional development of the testis by treatment with estrogen or a combined use of estrogen and androgen in neonatal/infantile males using extended drug delivery methods, for the purpose of inhibiting the production of testosterone (T), which causes a male-specific behavior and odor.

Definitions

In this document, the terms "a" or "an" are used to include one or more than one and the term; "or" is used to refer to a nonexclusive "or" unless otherwise indicated. In addition, the phraseology or terminology employed herein and not otherwise defined is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Reference in the specification to "one embodiment," "an embodiment," "an example embodiment," etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Values expressed in a range format should be interpreted in a flexible manner to include not only the numerical values explicitly recited as the limits of the range but also to include all the individual numerical values or sub-ranges encompassed within that range as if each numerical value and sub-range is explicitly recited. For example, a concentration range of "about 0.1% to about 5%" should be interpreted to include not only the explicitly recited concentration of about 0.1 wt. % to about 5 wt. %, but also the individual concentrations (e.g., 1%, 2%, 3%, and 4%) and the sub-ranges (e.g., 0.1% to 0.5%, 1.1% to 2.2%, and 3.3% to 4.4%) within the indicated range.

The term "about" as used herein can allow for a degree of variability in a value or range—for example, within 10%, within 5%, within 1%, within 0.5%, within 0.1%, within 0.05%, within 0.01%, within 0.005%, or within 0.001% of a stated value or of a stated limit of a range- and includes the exact stated value or range.

As used herein, an "effective amount" means an amount sufficient to inhibit the production of male-specific odor causing molecules. An effective amount can be administered in one or more administration. In some embodiments, an effective amount of estrogen and androgen can be achieved in conjunction with another drug, compound, or pharmaceutical composition. In other embodiments, an effective amount of estrogen and androgen may be achieved in isolation from the use of another drug, compound, or pharmaceutical composition.

The terms "carrier," "pharmaceutically acceptable carrier," or "physiologically acceptable carrier" as used herein refer to one or more formulation materials suitable for accomplishing or enhancing the delivery of estrogen and androgen as composition (i.e., pharmaceutical composition). Compositions and Methods There has been considerable effort to find a replacement for the physical castration procedure in ruminants, with animal welfare being one of the major concerns (4, 33). However, finding an alternative that could replace the procedure must take into consideration several potential organ targets that could disrupt the production of androgens, including the hypothalamus, pituitary and testis.

Inhibition Target 1. Hypothalamus and Pituitary. The invention is centered around a pharmaceutical intervention that inhibits development of the testes. In mammals, reproduction is regulated by hormones that are released from the Hypothalamus region of the brain, the nearby Pituitary gland, and the Gonads that must be exposed to pituitary hormones via blood circulation. This physiological system is known as the HPG axis. In this system, a hormone produced in one organ of the HPG axis either stimulates or inhibits the secretion of a hormone in another organ through regulatory loops, respectively known as positive and negative feedback loop. Hypothalamic neurons produce two key reproductive hormones, Kisspeptin (KISS1) and GnRH (Gonadotropin-Releasing Hormone) (34, 35, 36, 37). In a unidirectional regulation, KISS1 is secreted, binds to the KISS1 receptor (GPR54) in the cell membrane of the GnRH neurons, triggering the release of GnRH. Notably, if either the Kiss1 or Gpr54 gene is removed, it results in hypogonadism and sterility (38, 39). GnRH travels to the pituitary via a local portal vein and triggers the secretion of LH (luteinizing hormone) and FSH (follicle-stimulating hormone). Collectively, these peptide hormones stimulate the gonads to grow and produce sex steroids, primarily T, and to promote the production and release of sperm. This essential role of the Kisspeptin neurons in reproduction is conserved in ruminants (40, 41, 42, 43, 44).

In the hypothalamus, the target is the neuropeptide KISS1 produced by Kisspeptin neurons. This peptide initiates puberty by directly stimulating the release of GnRH (45, 46, 47) and thereby releasing LH from the pituitary to stimulate Leydig cells in the testis. Therefore, KISS1 plays a crucial role in the development of testes and the facilitation of appropriate timing of puberty. In support, mutation of either the Kiss1 gene, which encodes KISS1, or its receptor, GPR54 resulted in sterility in both male and female mice (39, 48, 49, 50, 51, 52). In the male, the loss of Kiss1 expression results in significantly lower plasma levels of LH and T, which produces male infertility (53, 54).

Estrogen receptor-1 (ESR1) and androgen receptor (AR) are both expressed in various cells of the hypothalamus (55, 56, 57) and thus both estrogen and androgens have potential influence over the development of the hypothalamus/pituitary pathway. Temporary treatment with exogenous estrogen targets the hypothalamus Kisspeptin neurons, permanently reducing KISS1 expression and subsequently GnRH and LH secretions, eventually lowering testicular T production and serum T levels (58). However, estrogen treatment alone in the neonatal bull was not sufficient to achieve long-term reduction in LH and T (59), possibly due to the use of a low dose or insufficient length of time exposure. Neonatal treatment with a synthetic androgen, such as Trenbolone or TBA or DHT, targets the pituitary directly and thus also helps to inhibit LH release by making the pituitary insensitive to GnRH stimulation (60, 61, 62). Therefore, for this innovation, the neonatal and infantile period of treatment includes a higher dose of estrogen, as well as an androgen as an active pharmaceutical ingredient (API), because together they will inhibit hypothalamus Kisspeptin neuron development and the pituitary gonadotrophic cell's release of LH, respectively.

In ruminants, there is also evidence that androgens, in addition to estrogens, are capable of having a strong inhibition of kisspeptin neurons, because in the castrate male the number of kisspeptin-immunolocalized cells is increased substantially (63). Also, androgens appear to have their major effects on the pituitary, where they inhibit LH release (64).

Inhibition Target 2: Testis. The core organs of the male reproductive system are the testes, which undergo dramatic developmental and structural changes from birth to puberty. Testicular development produces four major cell types: 1) germ cells surrounded and nurtured by 2) Sertoli cells, which with germ cells compose the seminiferous tubules; 3) thin, peritubular myoid cells that surround a basement membrane of the seminiferous tubule; and 4) Leydig cells, located between the tubules and blood vessels (65, 66, 67).

In the testis, Leydig cells are the major androgen producing cells. They serve as the source of T synthesis (68), with distinctive increases in T from birth to puberty (8, 69, 70). However, normal Sertoli cell development is also required for proper proliferation and differentiation of Leydig cells (71, 72, 73, 74, 75). Ruminant testes do not express the estrogen receptor (76, 77, 78), in contrast to the nonruminant species, in which Leydig cells, and sometimes Sertoli cells (79), express ESR1 and show estrogen responsiveness. However, Leydig cells of the ruminant testis do express AR and thus would be responsive to treatment with a potent androgen during the neonatal/infantile period. During development, Leydig cells depend on a number of factors for their stimulation, the primary one being the gonadotropin LH (80); however, Leydig cell maturation from progenitor and immature cells can be stimulated by androgens through local autocrine regulation (81). Therefore, a potent, androgen will also target the testes, if given during the neonatal/infantile period (69). This direct effect of an androgen would shift the cells away from proliferation and toward differentiation, while in the pituitary the androgen will inhibit LH release, the primary hormone necessary for Leydig cell stimulation, the promotion of cell proliferation and subsequent synthesis of androgens. However, treatment would be required during the neonatal/infantile period of development because waiting until after the infantile age (such as after more than 180 days of age in bulls) does not appear to be permanent, as the testes weights following TBA treatment at this older age showed no significant difference from non-treated bulls (82). Testicular development prior to birth is independent of the HPG axis. However, starting at birth, hormones from the HPG axisplay a vital role in regulatory control of testicular growth (54). The postnatal surge in serum T depends on the KISS1-stimulated secretion of GnRH and the subsequent release of LH (83). LH stimulates fetal Leydig cells to produce T, which is vital for masculinization of the young male (84, 85). Thus, the most effective reduction of testis production of androgen hormones requires the inhibition of Leydig cell development.

In addition to Leydig cells, during this neonatal/infantile period, Sertoli cells also experience a major stimulation of activity. In rodents, FSH is the primary stimulus of Sertoli cell proliferation during the neonatal/infantile period, which is essential for normal testis size. In rodents and ruminant males, it is well-established that FSH is a major driver for Sertoli cell proliferation and LH is the key factor in Leydig cell development (61, 86, 87, 88, 89). Sertoli cells nurture germ cells throughout spermatogenesis (90), but each Sertoli cell can supports only a finite number of germ cells (91). Thus, it is the total number of Sertoli cells that determines the ultimate size of the testis (71). Furthermore, the number of Sertoli cells indirectly regulates the number of Leydig cells (71, 73, 92). As such, the regulation of Sertoli cell numbers in the developing testis is just as important as inhibiting Leydig cell function.

Treatment residue. In the United States, it is important to ensure that any residual amount of the treatment hormones and the carrier in the treated animals would be below the level that is imposed or regulated by governing authorities such as the FDA and/or USDA. EB, a long-acting estrogen, when delivered at the right dose and over the optimum period during neonatal/infantile growth, will deliver permanent inhibition of the hypothalamus for reducing LH production. TBA is a synthetic androgen that has both direct effects on the testis and a more rapid inhibitory effect on pituitary release of LH. Thus, the combined treatment is capable of inhibiting all three components of the HPG axis and must be delivered neonatally through the neonatal/infantile period with extended, but temporary elevation of circulating levels of the compounds. This level of the compounds must be sufficient to inhibit Sertoli and Leydig cell proliferation and the onset of testicular maturation, while ensuring that the treatment compounds are depleted from the body at slaughter.

Currently, there are no non-surgical castration techniques available that have a high degree of certainty for both disrupting Kisspeptin neuron development or KISS1 expression, decreasing LH production, as well as directly inhibiting the development of testicular cellular components. Immunocastration inhibits the GnRH stimulation of LH production but must be given closer to puberty and requires repeated vaccination for sustained effects (93, 94, 95, 96). The proposed invention provides a simple, easy-to-implement, pharmaceutical intervention that can replace currently used procedures of surgical castration in newborn ruminants. A single, neonatal/infantile period injection of the two compounds in a sustained-release carrier will irreversibly inhibit activation of the HPG axis, inhibit Sertoli cell proliferation, and disrupt Leydig cell development and steroidogenic function of the testis. This treatment strategy will prevent the accumulation of the molecules that cause male-specific odor and block the development of aggression in male ruminants.

The drug pellet, microsphere, gel, or solution (hereafter, drug complex) comprises biocompatible-/biodegradable polymers or solvents.

The drug complex comprises a hormone-based compound configured to inhibit the postnatal release of LH from the pituitary, development of hypothalamic Kisspeptin neurons and cellular components of the testis.

The drug complex allows for the sustained but temporary release of the steroids into a body of an animal once the drug-carrier has been injected or implanted therein.

Embodiments of the invention comprise insertion methods configured to allow injection of a drug complex through larger epidermal layers or muscle.

In some embodiments of the invention, the drug complex may comprise EB and TBA. In other embodiments, the drug complex may comprise other estrogen esters and other forms of androgens. In some embodiments, the drug complex is injected into the subject within the first week after birth when animals are receiving vaccines and other shots.

Embodiments of the invention may include farm ruminants such as cattle, sheep, goats, deer, antelope, camels, and other livestock; while other embodiments of the invention may further include subjects such as horses and other physiologically similar to said subjects.

The invention involves the inhibition of testicular development and thereby the prevention of a rise in blood and tissue androgens (T) by treating neonatal/infantile males with a combination of a long-acting estrogen and an androgen in a delivery method that allows for sustained, but temporary elevation of the compounds during the neonatal/infantile period of growth. The combined steroids, estrogen and androgen, permit the targeting of both the hypothalamus/pituitary region, as well as the testis directly (both Sertoli and Leydig cells).

Concentration/Amount of Estrogen and/or Androgen

Male-specific odor and aggression inhibiting compositions comprise of estrogen and androgen. An effective amount of estrogen and androgen to induce the required inhibition of testis development and androgen production can depend, for example, the route of administration, the age of the animal, and its size (body weight). Accordingly, the skilled artisan may titer the dosage and modify the route of administration of estrogen and androgen to obtain the optimal effect for a particular animal.

A typical dosage of estrogen (EB as an example) may range from about 1 mg/kg to up to about 30 mg/kg or more. In other embodiments, the dosage of EB may range from 1 mg/kg up to about 30 mg/kg; or 5 mg/kg up to about 30 mg/kg; or 10 mg/kg up to about 30 mg/kg; or 20 mg/kg up to about 30 mg/kg.

A typical dosage of androgen (TBA, as an example) may range from about 50 mg/kg to up to about 200 mg/kg or more. In other embodiments, the dosage of androgen may range from 50 mg/kg up to about 200 mg/kg; or 70 mg/kg up to about 200 mg/kg; or 100 mg/kg up to about 200 mg/kg.

Timing of Administration

Compositions comprising estrogen and androgen to reduce male-specific odor and/or aggression are administered prior to puberty (prior to reaching sexual maturity/capable of reproduction). The compositions can be administered neonatally through the infantile period of growth (69). Administration of estrogen and androgen effectively inhibits/blocks maturation of sex organs/gonads in males.

Route of Administration

The route of administration of the composition provided herein is in accordance with known methods, e.g., injection (intraperitoneal, intramuscular, subcutaneous) and nasal (inhalation). In one embodiment, estrogen and androgen is administered for inhibition of male-specific odor and/or aggression of an animal in a single, one-time dose. In other embodiments, multiple administrations of estrogen and androgen can be carried out to inhibit testis development, male-specific odor and/or aggression.

Compositions

In one embodiment, estrogen and androgen compositions for injectable administration can be in the form of oleaginous suspensions, including oil, such as vegetable oil (e.g., corn oil), cottonseed oil, peanut oil, and/or sesame oil. Other carriers or fillers can be used instead of, or in addition to, oil. Carriers/fillers can include lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol. These suspensions can be formulated according to methods available to the art for dispersing and suspending ingredients.

In another embodiment, the composition described above can be encapsulated for administration. In one embodiment, a capsule can be formed from silicone tubing with plugs at each end to contain a mixture of, for example, estrogen, androgen and oil. The capsules can be placed, such as by injection (further described below), in the body of the subject. The estrogen and androgen compositions described herein can be formulated for immediate release or in a time release formulation (e.g., slow release). For example, estrogen and androgen can be prepared with carriers that protect estrogen and androgen against rapid release, such as a controlled release formulation.

Many methods for the preparation of controlled/slow-release formulations are known to those skilled in the art. For example, techniques for formulating a variety of sustained- or controlled-delivery means, such as liposome carriers, polymers (e.g., ethylene vinyl acetate, polyanhydrides, silicone, polyglycolic acid, collagen, polyorthoesters, polylactic acid and polylactic, polyglycolic copolymers (PLG), microparticles, nanoparticles (such as nanospheres, including biodegradable nanospheres or porous beads, and depot injections), a water insoluble polymer and a polyethylene glycol as a water-soluble pore forming agent, or with carrier/matrix such as cholesterol, magnesium stearate, ethyl cellulose N200 carrier/matrix are also known to those skilled in the art. For example, see PCT/US93/00829, which describes controlled release of porous polymeric microparticles for the delivery of pharmaceutical compositions. Additional examples of sustained-release preparations include semipermeable polymer matrices in the form of shaped articles, e.g., films or microcapsules. Sustained release matrices may include polyesters, hydrogels, polylactides (U.S. Pat. No. 3,773,919, EP 58,481), copolymers of L-glutamic acid and gamma ethyl-L-glutamate (97), poly (2-hydroxyethyl-methacrylate) (98, 99), ethylene vinyl acetate or poly-D(–)-3-hydroxybutyric acid (EP 133,988). Sustained-release compositions also include liposomes, which can be prepared by any of several methods known in the art. See e.g., Eppstein et al., (100), 1985; EP 36,676; EP 88,046; EP 143,949.

Controlled-release, slow release, or sustained-release refer to the release of an active ingredient, such as estrogen and androgen, from a composition or dosage form in which the active ingredient is released over an extended period of time. In one embodiment, controlled-release results in dissolution over several hours to a few days or weeks. In another embodiment, APIs are released over a period of a few months, including about 1 to 4 months. In another embodiment, APIs are released over an infantile period of growth.

In another embodiment, the composition is formulated for inhalation; for example, EB and TBA can be formulated as a dry powder. Inhalation solutions may also be formulated with a propellant for aerosol delivery. In another embodiment, inhalation solutions may be nebulized.

One embodiment provides kits for producing a single-dose administration unit. The kits may contain single and multi-chambered pre-filled syringes containing estrogen and androgen and instructions for use (inhibiting testis development and reducing male-specific odor).

EXAMPLES

Example 1—Effects of Injecting EB+TBA in Neonatal Piglets Via Carrier on the Serum LH Level Treatment of animals. EB+TBA injectable implant contains EB 7 mg and TBA 50 mg EB (n=4) was implanted to neonatal male piglets (Large White X Landrace) on day 1 after birth by subcutaneous injection on the backside of the neck. The injection site of the implants was then sealed using surgical sealant. All piglets were raised in the same pen and blood was collected on week 3 to measure the concentrations of LH.

LH measurement. Serum LH levels were measured by Pig LH ELISA (LS-F34361, LSBio Inc., WA). Data are presented using descriptive analysis as well as mean±SD.

Results. Control intact animals (n=3) had 23.7±15.86 ng/mL serum LH concentration at 3 weeks of age (FIG. 1). In contrast, animals treated with EB-alone had 97% (0.75±0.17 ng/mL) lower serum LH concentrations than control intact animals.

The function of the pituitary gonadotropic cells, especially synthesis and secretion of LH, is crucial for gonad development and steroidogenesis. This result shows that EB+TBA effectively inhibit the LH production in pigs.

Example 2—Effects of Injecting EB+TBA in Neonatal Piglets Via Carrier on the Testis Development and Function in Slaughter Age Treatment of animals. EB+TBA injectable implant contains EB 14 mg and TBA 100 mg EB (n=4) was implanted to neonatal male piglets (Large White X Landrace) on day 1 after birth by subcutaneous injection on the backside of the neck. The injection site of the implants was then sealed using the surgical sealant. All piglets were raised in the same pen until 26 weeks of age, testes weight was measured at the end of the experiment. For the hormone measurement, blood was collected at the same time.

Testis weight and testosterone levels. Testes were collected from 26-weeks-old boars and their weight was measured. Data are presented using descriptive analysis as well as mean±SD of average testis weight in each individual. At the same time, blood was collected from each individual, and serum was separated by centrifugation. Serum testosterone level was measured by Testosterone ELISA kit (EIA1559, DRG International Inc.) and data are presented using descriptive analysis as well as mean±SD of ng/mL testosterone.

Results. Control intact animals (n=3) showed 637.5±91.02 g testis weight and 11.53±5.31 ng/mL of serum testosterone levels. Animals treated with EB+TBA had 63.9% lower testis weight (230.0±50.32 g) and 49.1% lower serum testosterone levels (5.85±1.38 ng/mL) compared to those of Intact. This indicates that neonatal treatment of EB+TBA inhibits the testis development and steroidogenic activity of testicular cells until slaughtering age.

Example 3—Effects of Injecting EB+TBA in Neonatal Goats Via Carrier on the Testis Development and Function in Slaughter Age (4-5-Month-Old)

Treatment of animals. EB+TBA injectable implant contains EB 14 mg and TBA 100 mg or EB 28 mg and TBA 200 mg was implanted to neonatal male goats on day 1-3 after birth by subcutaneous injection on the backside of the neck. The injection site of the implants was then sealed using the surgical sealant. Testes size was measured by Vanier calipers at 3-5 months of age and volume was calculated based on the formula width×depth×length (cm$^3$). Serum testosterone levels were measured by Testosterone ELISA kits (EIA1559, DRG International Inc.) at 4-5 months of age. Data are presented as mean±SD of testis size and serum testosterone level in each individual.

Results. Control intact animals (n=3) showed 184.45±55.91 cm$^3$ (width×depth×length) testis size. Animals treated with EB 14 mg+TBA 100 mg (n=5) and EB 28 mg+TBA 200 mg (n=4) had 60.2% (73.42±11.35 cm$^3$) and 76.4% (43.46±25.08 cm$^3$) smaller testis size compared to those of Intact, respectively. In the measurement of serum testosterone levels, Control intact animals (n=3) showed 0.59±0.52 ng/mL of serum testosterone levels. EB 14 mg+TBA 100 mg (n=3) and EB 28 mg+TBA 200 mg (n=3) had 79.7% (0.12±0.15 ng/mL) and 94.9% (0.03±0.00 ng/mL) lower testosterone levels compared to intact animals. This indicates that neonatal treatment of EB+TBA inhibits the testis development and steroidogenic activity of testicular cells.

BIBLIOGRAPHY

1. Price E O, Adams T E, Huxsoll C C, Borgwardt R E. Aggressive behavior is reduced in bulls actively immunized against gonadotropin-releasing hormone. J Anim Sci. 2003; 81(2):411-5.
2. Cronin G, Dunshea F, Butler K, McCauley I, Barnett J, Hemsworth P. The effects of immuno- and surgical-castration on the behaviour and consequently growth of group-housed, male finisher pigs. Appl Anim Behav Sci. 2003; 81(2):111-26.

3. Seideman S, Cross H, Oltjen R, Schanbacher B. Utilization of the intact male for red meat production: a review. J Anim Sci. 1982; 55(4):826-40.

4. Needham T, Lambrechts H, Hoffman L C. Castration of male livestock and the potential of immunocastration to improve animal welfare and production traits: Invited Review. South African Journal of Animal Science. 2017; 47:731-42.

5. Bouissou M F. Androgens, Aggressive Behaviour and Social Relationships in Higher Mammals. Hormone Research in Paediatrics. 1983; 18(1-3):43-61.

6. Cunningham R L, Lumia A R, McGinnis M Y. Androgen Receptors, Sex Behavior, and Aggression. Neuroendocrinology. 2012; 96(2):131-40.

7. Huxsoll C C, Price E O, Adams T E. Testis function, carcass traits, and aggressive behavior of beef bulls actively immunized against gonadotropin-releasing hormone. J Anim Sci. 1998; 76(7):1760-6.

8. Kiyma Z, Adams T E, Hess B W, Riley M L, Murdoch W J, Moss G E. Gonadal function, sexual behavior, feedlot performance, and carcass traits of ram lambs actively immunized against GnRH. J Anim Sci. 2000; 78(9):2237-43.

9. Marti S, Devant M, Amatayakul-Chantler S, Jackson J A, Lopez E, Janzen E, et al. Effect of anti-gonadotropin-releasing factor vaccine and band castration on indicators of welfare in beef cattle. Journal of Animal Science. 2015; 93:1581.

10. Tennessen T, Price M A, Berg R T. The Social Interactions of Young Bulls and Steers after Re-Grouping. Appl Anim Behav Sci. 1985; 14(1):37-47.

11. Imwalle D B, Schillo K K. Castration increases pulsatile luteinizing hormone release, but fails to diminish mounting behavior in sexually experienced bulls. Domest Anim Endocrinol. 2002; 22(4):223-35.

12. Katz L S. Sexual behavior of domesticated ruminants. Horm Behav. 2007; 52(1):56-63.

13. Morlein D, Trautmann J, Gertheiss J, Meier-Dinkel L, Fischer J, Eynck H J, et al. Interaction of Skatole and Androstenone in the Olfactory Perception of Boar Taint. J Agric Food Chem. 2016; 64(22):4556-65.

14. Bonneau M, Kempster A J, Claus R, Claudi-Magnussen C, Diestre A, Tornberg E, et al. An international study on the importance of androstenone and skatole for boar taint: I. Presentation of the programme and measurement of boar taint compounds with different analytical procedures. Meat Sci. 2000; 54(3):251-9.

15. Patterson R L S. 5α-androst-16-ene-3-one:—Compound responsible for taint in boar fat. J Sci Food Agric. 1968; 19(1):31-8.

16. Shirasu M, Yoshikawa K, Takai Y, Nakashima A, Takeuchi H, Sakano H, et al. Olfactory Receptor and Neural Pathway Responsible for Highly Selective Sensing of Musk Odors. Neuron. 2014; 81(1):165-78.

17. Fan M, Zhang M, Shi M, Zhang T, Qi L, Yu J, et al. Sex hormones play roles in determining musk composition during the early stages of musk secretion by musk deer (<i>Moschus berezovskii</i>). Endocrine Journal. 2018; 65(11):1111-20.

18. Gorraiz C, Beriain M J, Chasco J, Insausti K. Effect of Aging Time on Volatile Compounds, Odor, and Flavor of Cooked Beef from Pirenaica and Friesian Bulls and Heifers. Journal of Food Science. 2002; 67(3):916-22.

19. Arshad M S, Sohaib M, Ahmad R S, Nadeem M T, Imran A, Arshad M U, et al. Ruminant meat flavor influenced by different factors with special reference to fatty acids. Lipids in Health and Disease. 2018; 17(1):223.

20. Guerrero A, Valero M V, Campo M M, Sañudo C. Some factors that affect ruminant meat quality: from the farm to the fork. Review. Acta Scientiarum Animal Sciences [online]. 2013; 35(4):335-47.

21. Zhang C, Zhang H, Liu M, Zhao Xg, Luo H. Effect of Breed on the Volatile Compound Precursors and Odor Profile Attributes of Lamb Meat. Foods. 2020; 9(9):1178.

22. Ames J M, Sutherland M M. Effect of Castration and Slaughter Age on the Flavor of Sheepmeat. In: Xiong Y L, Chi-Tang H, Shahidi F, editors. Quality Attributes of Muscle Foods. Boston, MA: Springer US; 1999. p. 147-57.

23. Young O A, Reid D H, Smith M E, Braggins T J. Sheepmeat odour and flavour. In: Shahidi F, editor. Flavor of Meat and Meat Products. Boston, MA: Springer US; 1994. p. 71-97.

24. Sutherland M M, Ames J M. Free Fatty Acid Composition of the Adipose Tissue of Intact and Castrated Lambs Slaughtered at 12 and 30 Weeks of Age. Journal of Agricultural and Food Chemistry. 1996; 44(10):3113-6.

25. Kang G, Cho S, Seong P, Kang S, Park K, Park B, et al. Comparisons of Meat Quality Characteristics between Castration and Non-castration from Dairy Goats: □ □ □ □ □ □ □ □ □ □ □ □ □ □ □ □. Korean J Food Sci An. 2013; 33(1):119-24.

26. Nagamine I, Sunagawa K. Effects of the castration on the growth, meat production and odors in male goats. Animal Behaviour and Management. 2017; 53(4):137-50.

27. Zamiri M J, Eilami B, Kianzad M R. Effects of castration and fattening period on growth performance and carcass characteristics in Iranian goats. Small Ruminant Research. 2012; 104(1):55-61.

28. Rust R L, Thomson D U, Loneragan G H, Apley M D, Swanson J C. Effect of different castration methods on growth performance and behavior responses of postpubertal beef bulls. The Bovine Practitioner. 2007; 41(2):111-9.

29. Stilwell G, Lima M S, Broom D M. Effects of nonsteroidal anti-inflammatory drugs on long-term pain in calves castrated by use of an external clamping technique following epidural anesthesia. Am J Vet Res. 2008; 69(6):744-50.

30. Fordyce G, Hodge P B, Beaman N J, Laing A R, Campero C, Shepherd R K. An evaluation of calf castration by intra-testicular injection of a lactic acid solution. Aust Vet J. 1989; 66(9):272-6.

31. Monleon E, Noya A, Carmen Garza M, Ripoll G, Sanz A. Effects of an anti-gonadotrophin releasing hormone vaccine on the morphology, structure and function of bull testes. Theriogenology. 2020; 141:211-8.

32. Fisher A D, Crowe M A, Alonso de la Varga M E, Enright W J. Effect of castration method and the provision of local anesthesia on plasma cortisol, scrotal circumference, growth, and feed intake of bull calves. J Anim Sci. 1996; 74(10):2336-43.

33. Yamada P H, Codognoto V M, Rydygier de Ruediger F, Mayara da Silva K, Aristizabal V V, Kastelic J P, et al. A comparison of immunological, chemical and surgical castration of Nelore bulls. Theriogenology. 2021; 169:9-13.

34. Tomikawa J, Homma T, Tajima S, Shibata T, Inamoto Y, Takase K, et al. Molecular characterization and estrogen regulation of hypothalamic KISS1 gene in the pig. Biology of reproduction. 2010; 82(2):313-9.

35. Scott C J, Rose J L, Gunn A J, McGrath B M. Kisspeptin and the regulation of the reproductive axis in domestic animals. J Endocrinol. 2019; 240:R1-R16.

36. Yeo S H, Colledge W H. The Role of Kiss1 Neurons As Integrators of Endocrine, Metabolic, and Environmental Factors in the Hypothalamic-Pituitary-Gonadal Axis. Front Endocrinol (Lausanne). 2018; 9:188.

37. Yeo S H, Kyle V, Blouet C, Jones S, Colledge W H. Mapping neuronal inputs to Kiss1 neurons in the arcuate nucleus of the mouse. PLoS One. 2019; 14(3):e0213927.

38. Novaira H J, Sonko M L, Hoffman G, Koo Y, Ko C, Wolfe A, et al. Disrupted kisspeptin signaling in GnRH neurons leads to hypogonadotrophic hypogonadism Mol Endocrinol. 2014; 28(2):225-38.

39. d'Anglemont de Tassigny X, Fagg L A, Dixon J P, Day K, Leitch H G, Hendrick A G, et al. Hypogonadotropic hypogonadism in mice lacking a functional Kiss1 gene. Proceedings of the National Academy of Sciences of the United States of America. 2007; 104(25):10714-9.

40. Smith J T, Clay C M, Caraty A, Clarke I J. KiSS-1 messenger ribonucleic acid expression in the hypothalamus of the ewe is regulated by sex steroids and season. Endocrinology. 2007; 148(3):1150-7.

41. Smith J T, Li Q, Yap K S, Shahab M, Roseweir A K, Millar R P, et al. Kisspeptin is essential for the full preovulatory LH surge and stimulates GnRH release from the isolated ovine median eminence. Endocrinology. 2011:152(3):1001-12.

42. Roseweir A K, Kauffman A S, Smith J T, Guerriero K A, Morgan K, Pielecka-Fortuna J, et al. Discovery of potent kisspeptin antagonists delineate physiological mechanisms of gonadotropin regulation. J Neurosci. 2009; 29(12):3920-9.

43. Whitlock B K, Daniel J A, Wilbom R R, Maxwell H S, Steele B P, Sartin J L. Interaction of kisspeptin and the somatotropic axis. Neuroendocrinology. 2010; 92(3):178-88.

44. Ezzat Ahmed A, Saito H, Sawada T, Yaegashi T, Yamashita T, Hirata T, et al. Characteristics of the stimulatory effect of kisspeptin-10 on the secretion of luteinizing hormone, follicle-stimulating hormone and growth hormone in prepubertal male and female cattle. J Reprod Dev. 2009; 55(6):650-4.

45. Cortes M E, Carrera B, Rioseco H, Pablo del Rio J, Vigil P. The Role of Kisspeptin in the Onset of Puberty and in the Ovulatory Mechanism: A Mini-review. J Pediatr Adolesc Gynecol. 2015; 28(5):286-91.

46. Terasawa E, Guerriero K A, Plant T $T_M$. Kisspeptin and puberty in mammals. Adv Exp Med Biol. 2013; 784:253-73.

47. Uenoyama Y, Inoue N, Nakamura S, Tsukamura H. Central Mechanism Controlling Pubertal Onset in Mammals: A Triggering Role of Kisspeptin. Front Endocrinol (Lausanne). 2019; 10:312.

48. Seminara S B, Messager S, Chatzidaki E E, Thresher R R, Acierno J S, Jr., Shagoury J K, et al. The GPR54 gene as a regulator of puberty. N Engl J Med. 2003; 349(17):1614-27.

49. Messager S, Chatzidaki E E, Ma D, Hendrick A G, Zahn D, Dixon J, et al. Kisspeptin directly stimulates gonadotropin-releasing hormone release via G protein-coupled receptor 54. Proceedings of the National Academy of Sciences of the United States of America. 2005:102(5):1761-6.

50. Funes S, Hedrick J A, Vassileva G, Markowitz L, Abbondanzo S, Golovko A, et al. The KiSS-1 receptor GPR54 is essential for the development of the murine reproductive system. Biochem Biophys Res Commun. 2003; 312(4):1357-63.

51. Ikegami K, Goto T, Nakamura S, Watanabe Y, Sugimoto A, Majarune S, et al. Conditional kisspeptin neuron-specific Kiss1 knockout with newly generated Kiss1-floxed and Kiss1-Cre mice replicates a hypogonadal phenotype of global Kiss1 knockout mice. J Reprod Dev. 2020; 66(4):359-67.

52. Lapatto R, Pallais J C, Zhang D, Chan Y M, Mahan A, Cerrato F, et al. Kiss1-/- mice exhibit more variable hypogonadism than Gpr54-/- mice. Endocrinology. 2007; 148(10):4927-36.

53. Minabe S, Nakamura S, Fukushima E, Sato M, Ikegami K, Goto T, et al. Inducible Kiss1 knockdown in the hypothalamic arcuate nucleus suppressed pulsatile secretion of luteinizing hormone in male mice. J Reprod Dev. 2020.

54. Chen J, Minabe S, Munetomo A, Magata F, Sato M, Nakamura S, et al. Kiss1-dependent and independent release of luteinizing hormone and testosterone in perinatal male rats. Endocr J. 2022.

55. Walker D M, Kirson D, Perez L F, Gore A C. Molecular profiling of postnatal development of the hypothalamus in female and male rats. Biology of reproduction. 2012; 87(6):129.

56. Brock O, De Mees C, Bakker J. Hypothalamic expression of oestrogen receptor α and androgen receptor is sex-, age- and region-dependent in mice. J Neuroendocrinol. 2015; 27(4):264-76.

57. de Souza F S, Nasif S, Lopez-Leal R, Levi D H, Low M J, Rubinsten M. The estrogen receptor alpha colocalizes with proopiomelanocortin in hypothalamic neurons and binds to a conserved motif present in the neuron-specific enhancer nPE2. Eur J Pharmacol. 2011; 660(1):181-7.

58. Minabe S, Sato M, Inoue N, Watanabe Y, Magata F, Matsuda F, et al. Neonatal Estrogen Causes Irreversible Male Infertility via Specific Suppressive Action on Hypothalamic Kiss1 Neurons. Endocrinology. 2019; 160(5):1223-33.

59. Bass J J, Peterson A J, Payne E, Jarnet M P. The effect of neonatal estrogen treatment on plasma hormone levels and behaviour in pre- and post-pubertal bulls. Theriogenology. 1977; 8(1):59-71.

60. Gettys T W, D'Occhio M J, Henricks D M, Schanbacher B D. Suppression of LH secretion by oestradiol, dihydrotestosterone and trenbolone acetate in the acutely castrated bull. J Endocrinol. 1984; 100(1):107-12.

61. Schanbacher B D, Johnson M P, Tindall D J. Androgenic regulation of luteinizing hormone secretion: relationship to androgen binding in sheep pituitary. Biology of reproduction. 1987; 36(2):340-50.

62. Godfrey R W, Lunstra D D, Schanbacher B D. Effect of implanting bull calves with testosterone propionate, dihydrotestosterone propionate or oestradiol-17 beta prepubertally on the pituitary-testicular axis and on postpubertal social and sexual behaviour. J Reprod Fertil. 1992; 94(1):57-69.

63. Matsuyama S, Ohkura S, Mogi K, Wakabayashi Y, Mori Y, Tsukamura H, et al. Morphological Evidence for Direct Interaction between Kisspeptin and Gonadotropin-Releasing Hormone Neurons at the Median Eminence of the Male Goat: An Immunoelectron Microscopic Study. Neuroendocrinology. 2011; 94(4):323-32.

64. Kennedy R I, Rawlings N C, Murphy B D. The effects of androgens and gonadotropins on testicular development in the prepubertal rat. Can J Comp Med. 1985; 49(3):333-6.

65. Hess R A. Small tubules, surprising discoveries: from efferent ductules in the turkey to the discovery that estrogen receptor alpha is essential for fertility in the male. Anim Reprod. 2015; 12(1):7-23.

66. Lara N L M, Costa G M J, Avelar G F, Lacerda S M S N, Hess R A, de França L R. Testis Physiology—Overview and Histology. In: Skinner M K, editor. Encyclopedia of Reproduction (Second Edition). 1. San Diego: Academic Press: Elsevier; 2018. p. 105-16.

67. Lara N L M, Avelar G F, Costa G M J, Lacerda S M S N, Hess R A, de França L R. Cell-Cell Interactions-Structural. In: Skinner M K, editor. Encyclopedia of Reproduction (Second Edition). 1. Oxford: Academic Press; 2018. p. 68-75.

68. Zirkin B R, Papadopoulos V. Leydig cells: formation, function, and regulation. Biol Reprod. 2018; 99(1):101-11.

69. Amann R P, Walker O A. Changes in the pituitary-gonadal axis associated with puberty in Holstein bulls. J Anim Sci. 1983; 57(2):433-42.

70. Moura A A, Erickson B H. Age-related changes in peripheral hormone concentrations and their relationships with testis size and number of Sertoli and germ cells in yearling beef bulls. Reproduction. 1997; 111(2):183-90.

71. Rebourcet D, Darbey A, Monteiro A, Soffientini U, Tsai Y T, Handel I, et al. Sertoli Cell Number Defines and Predicts Germ and Leydig Cell Population Sizes in the Adult Mouse Testis. Endocrinology. 2017; 158(9):2955-69.

72. Chen M, Wang X, Wang Y, Zhang L, Xu B, Lv L, et al. Wt1 is involved in leydig cell steroid hormone biosynthesis by regulating paracrine factor expression in mice. Biology of reproduction. 2014; 90(4).

73. Rebourcet D, O'Shaughnessy P J, Pitetti J L, Monteiro A, O'Hara L, Milne L, et al. Sertoli cells control peritubular myoid cell fate and support adult Leydig cell development in the prepubertal testis. Development. 2014; 141(10):2139-49.

74. De Gendt K, Atanassova N, Tan K A, de Franca L R, Parreira G G, McKinnell C, et al. Development and function of the adult generation of Leydig cells in mice with Sertoli cell-selective or total ablation of the androgen receptor. Endocrinology. 2005; 146(9):4117-26.

75. Kothandapani A, Larsen M C, Lee J, Jorgensen J S, Jefcoate C R. Distinctive functioning of STARD1 in the fetal Leydig cells compared to adult Leydig and adrenal cells. Impact of Hedgehog signaling via the primary cilium. Mol Cell Endocrinol. 2021; 531:111265.

76. Goyal H O, Bartol F F, Wiley A A, Khalil M K, Williams C S, Vig M M. Regulation of androgen and estrogen receptors in male excurrent ducts of the goat: an immunohistochemical study. Anat Rec. 1998; 250(2):164-71.

77. Mansour M M, Machen M R, Tarleton B J, Wiley A A, Wower J, Bartol F F, et al. Expression and molecular characterization of estrogen receptor alpha messenger RNA in male reproductive organs of adult goats. Biology of reproduction. 2001; 64(5):1432-8.

78. Antalikova J, Secova P, Horovska L, Krejcirova R, Simonik O, Jankovicova J, et al. Missing Information from the Estrogen Receptor Puzzle: Where Are They Localized in Bull Reproductive Tissues and Spermatozoa? Cells. 2020; 9(1):183.

79. Ramesh R, Pearl C A, At-Taras E, Roser J F, Berger T. Ontogeny of androgen and estrogen receptor expression in porcine testis: effect of reducing testicular estrogen synthesis. Anim Reprod Sci. 2007; 102(3-4):286-99.

80. Culty M, Papadopoulos V, Zirkin B. Leydig Cells: Fetal to Aged Testes. In: Skinner M K, editor. Encyclopedia of Reproduction (Second Edition). Oxford: Academic Press; 2018. p. 39-41.

81. Shi L, Li J, Tian F, Tang Y, Wang S, Li Q, et al. Dimethylbisphenol A inhibits the differentiation of stem Leydig cells in adult male rats by androgen receptor (NR3C4) antagonism. Toxicol Lett. 2022; 366:58-71.

82. Geary T W, Wells K J, deAvila D M, deAvila J, Conforti V A, McLean D J, et al. Effects of immunization against luteinizing hormone-releasing hormone and treatment with trenbolone acetate on reproductive function of beef bulls and steers. J Anim Sci. 2011; 89(7):2086-95.

83. Clarkson J, Herbison A E. Hypothalamic control of the male neonatal testosterone surge. Philos Trans R Soc Lond B Biol Sci. 2016; 371(1688):20150115.

84. O'Shaughnessy P J, Baker P, Sohnius U, Haavisto A M, Charlton H M, Huhtaniemi I. Fetal development of Leydig cell activity in the mouse is independent of pituitary gonadotroph function. Endocrinology. 1998; 139(3): 1141-6.

85. Klonisch T, Fowler P A, Hombach-Klonisch S. Molecular and genetic regulation of testis descent and external genitalia development. Dev Biol. 2004; 270(1):1-18.

86. MacDonald R D, Deaver D R, Schanbacher B D. Prepubertal changes in plasma FSH and inhibin in Holstein bull calves: responses to castration and(or) estradiol. Journal of Animal Science. 1991; 69(1):276-82.

87. Harstine B R, Cruppe L H, Abreu F M, Rodrigues A D, Premanandan C, DeJarnette J M, et al. Impact of a timed-release FSH treatment from 2 to 6 months of age in bulls I: Endocrine and testicular development of beef bulls. Theriogenology. 2018; 105:142-9.

88. Oduwole O O, Huhtaniemi I T, Misrahi M. The Roles of Luteinizing Hormone, Follicle-Stimulating Hormone and Testosterone in Spermatogenesis and Folliculogenesis Revisited. Int J Mol Sci. 2021; 22(23).

89. Ramaswamy S, Weinbauer G F. Endocrine control of spermatogenesis: Role of FSH and LH/testosterone. Spermatogenesis. 2014; 4(2):e996025.

90. Mruk D D, Cheng C Y. Sertoli-Sertoli and Sertoli-germ cell interactions and their significance in germ cell movement in the seminiferous epithelium during spermatogenesis. Endocr Rev. 2004; 25(5):747-806.

91. Meroni S B, Galardo M N, Rindone G, Gorga A, Riera M F, Cigorraga S B. Molecular Mechanisms and Signaling Pathways Involved in Sertoli Cell Proliferation. Front Endocrinol (Lausanne). 2019; 10:224.

92. Rebourcet D, O'Shaughnessy P J, Monteiro A, Milne L, Cruickshanks L, Jeffrey N, et al. Sertoli cells maintain Leydig cell number and peritubular myoid cell activity in the adult mouse testis. PLoS One. 2014; 9(8):e105687.

93. Bolado-Sarabia J, Pérez-Linares C, Figueroa-Saavedra F, Tamayo-Sosa A, Barreras-Serrano A, Sánchez-López E, et al. Effect of immunocastration on behaviour and blood parameters (cortisol and testosterone) of Holstein bulls. Austral journal of veterinary sciences. 2018; 50:77-81.

94. Yamada P H, Codognoto V M, Rydygier de Ruediger F, Mayara da Silva K, Aristizabal V V, Kastelic J P, et al. A comparison of immunological, chemical and surgical castration of Nelore bulls. Theriogenology. 2021; 169.9-13.

US 12,691,126 B2

17

95. P R H, Vidal S, Larrain R, Saenz L. Effectiveness of a New Recombinant antiGnRH Vaccine for Immunocastration in Bulls. Animals (Basel). 2021; 11(5).
96. Hernandez-Medrano J H, Williams R W, Peters A R, Hannant D, Campbell B K, Webb R. Neonatal immunisation against a novel gonadotrophin-releasing hormone construct delays the onset of gonadal growth and puberty in bull calves. Reprod Fertil Dev. 2012; 24(7):973-82.
97. Sidman K R, Steber W D, Schwope A D, Schnaper G R. Controlled release of macromolecules and pharmaceuticals from synthetic polypeptides based on glutamic acid. Biopolymers. 1983; 22(1):547-56.
98. Langer R, Brem H, Tapper D. Biocompatibility of polymeric delivery systems for macromolecules. J Biomed Mater Res. 1981; 15(2):267-77.
99. Langer R. Controlled release of macromolecules. 1982.
100. Eppstein D A, Marsh Y V, van der Pas M, Feigner P L, Schreiber A B. Biological activity of liposome-encapsulated murine interferon gamma is mediated by a cell membrane receptor. Proc Natl Acad Sci USA. 1985; 82(11):3688-92.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof) or with respect to other examples (or one or more aspects thereof) shown or described herein.

In the event of inconsistent usages between this document and any documents so incorporated by reference, the usage in this document controls.

The above description is intended to be illustrative and not restrictive. For example, the above-described examples (or one or more aspects thereof) may be used in combination with each other. Other embodiments can be used, such as "by one of ordinary skill in the art" upon reviewing the above description. The Abstract is provided to comply with 37 C.F.R. § 1.72(b) to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in fewer than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims along with the full scope of equivalents to which such claims are entitled.

All publications, patents, and patent applications, Genbank sequences, websites and other published materials referred to throughout the disclosure herein are herein incorporated by reference to the same extent as if each individual publication, patent, or patent application, Genbank sequences, websites and other published materials was specifically and individually indicated to be incorporated by reference. In the event that the definition of a term incorporated by reference conflicts with a term defined herein, this specification shall control.

What is claimed is:
1. A method for inhibiting testicular development in ruminants, which prevents the pubertal rise in blood and tissue androgens, comprising administering to said ruminants an estrogen or a combination of an estrogen and an androgen within a few weeks or months after birth during the neonatal to infantile period.
2. The method of claim 1, wherein the administration is by subcutaneous injection, intra-muscular injection, or by nasal inhalation.
3. The method of claim 1, further comprising an implant wherein the implant comprises said estrogen and androgen.
4. The method of claim 1, wherein the estrogen and androgen target hypothalamus-pituitary axis and testis development, respectively.
5. The method of claim 3, wherein the implant comprises a material or enclosure that provides sustained release of the compounds during the neonatal/infantile period.
6. The method of claim 1, wherein the injected estrogen and androgen are not present in the blood or tissues when the animals are slaughtered.
7. The method of claim 5, wherein the material or enclosure that provides sustained release comprises biodegradable polymers or biocompatible materials.
8. The method of claim 5, wherein the material or enclosure that provides sustained release is a form of capsule, pellets, microspheres, gel, or solution.
9. The method of claim 1, wherein the estrogen is an estradiol ester, selected from the group consisting of estradiol benzoate (EB), estradiol valerate and estradiol cypionate, with the dose range of 1-30 mg/kg bodyweight.
10. The method of claim 1, wherein the androgen is selected from the group consisting of testosterone, testosterone esters, 5α-dihydrotestosterone, 5α-dihydrotestosterone esters, trenbolone and trenbolone esters with a dose range of 50-200 mg/kg bodyweight.
11. The method of claim 1, wherein the injected amount of the estrogen/androgen combination is in a dose sufficient to inhibit kisspeptin neurons in the hypothalamus, LH production in the pituitary, Sertoli cell proliferation in the testis and Leydig cell proliferation and production of androgens in the testis and odor-molecule accumulation in the fat and meat.
12. The method of claim 7, wherein the material or enclosure comprises silicone.

* * * * *